US006930586B2

(12) United States Patent
Tseung et al.

(10) Patent No.: US 6,930,586 B2
(45) Date of Patent: Aug. 16, 2005

(54) CARBON MONOXIDE DETECTOR

(75) Inventors: Alfred Chan Chung Tseung, London (GB); Darren Paul Lapham, Benfleet (GB); Xuekang Shan, London (GB); Ian Colbeck, Colchester (GB)

(73) Assignee: Catalytic Electrodes Limited, London (GB)

( * ) Notice: Subject to any disclaimer, the term of this patent is extended or adjusted under 35 U.S.C. 154(b) by 0 days.

(21) Appl. No.: 10/659,691

(22) Filed: Sep. 10, 2003

(65) Prior Publication Data

US 2004/0056754 A1 Mar. 25, 2004

Related U.S. Application Data

(63) Continuation of application No. 10/208,601, filed on Jul. 29, 2002, which is a continuation of application No. PCT/GB01/00334, filed on Jan. 29, 2001.

(30) Foreign Application Priority Data

Jan. 28, 2000  (GB) ............................................. 0002027
Feb. 9, 2000   (GB) ............................................. 0002808
Aug. 2, 2001   (WO) ................................... 01/55710 A1

(51) Int. Cl.$^7$ ............................................. H01C 7/00
(52) U.S. Cl. ........................ 338/34; 73/31.05; 73/31.01
(58) Field of Search .................... 338/34, 35; 73/31.05, 73/31.01

(56) References Cited

U.S. PATENT DOCUMENTS

| 3,528,857 A | * | 9/1970  | Oswin et al. ................. 429/40 |
| 3,951,603 A |   | 4/1976  | Obayashi et al. ............. 23/232 |
| 4,132,619 A | * | 1/1979  | Klein et al. ................. 204/242 |
| 4,146,438 A | * | 3/1979  | de Nora et al. ................ 205/43 |
| 4,221,827 A |   | 9/1980  | Parry et al. .................. 427/125 |
| 4,297,333 A | * | 10/1981 | Crawford et al. ........... 423/241 |
| 4,314,996 A |   | 2/1982  | Sekido et al. ................. 422/98 |
| 4,347,166 A | * | 8/1982  | Tosaki et al. ............. 252/521.2 |
| 4,413,502 A |   | 11/1983 | Ohta et al. ...................... 73/23 |
| 4,546,058 A | * | 10/1985 | Charkey et al. ............. 429/223 |
| 4,587,104 A |   | 5/1986  | Yannopoulos ................. 422/94 |
| 5,084,147 A | * | 1/1992  | Bianchi et al. ............. 205/348 |
| 5,351,029 A |   | 9/1994  | Huth et al. .................... 338/34 |
| 5,644,116 A |   | 7/1997  | Noda et al. ............. 204/157.15 |
| 5,793,276 A | * | 8/1998  | Tosaka et al. ............. 338/22 R |
| 5,879,943 A | * | 3/1999  | Ando et al. .................... 436/41 |
| 6,165,336 A | * | 12/2000 | Maki et al. .................. 204/415 |
| 6,379,529 B1 | * | 4/2002  | Wahl et al. ............... 205/780.5 |
| 6,522,237 B1 | * | 2/2003  | Ito et al. .................... 338/22 R |
| 6,533,909 B2 | * | 3/2003  | Duruz et al. ............. 204/243.1 |

OTHER PUBLICATIONS

Lennykh et al. abstract for SU 902082 patent (Jan. 1982).*
Chiu, C., et al., "The influence of microstructure and eposition methods on CO gas sensing properties of La0.8Sr0.2Co1–xxNixo3–? perovskite films", *Sensors and ACtuators B 54*, (1999), 236–242.
Satake, Kazuko, "CO Gas Sensing Element (Abstract)", *Patent Abstracts of Japan—JP 08 2200 45 A (Tokuyama Corp.)*, vol. 1996, No. 12, Dec. 26, 1996.

(Continued)

*Primary Examiner*—Karl D. Easthom
(74) *Attorney, Agent, or Firm*—Schwegman, Lundberg, Woessner & Kluth, P.A.

(57) ABSTRACT

A carbon monoxide (CO) detection unit incorporates a sensor which is a film or layer of $Ni_xCo_{1-x}O_y$ where x is from 0.1 to 0.9, e.g., spinel. The CO is detected by measuring the change in the electrical properties of the sensor. The detector can measure CO concentrations below 100 ppm and is capable of operating at room temperature and can be applied to domestic, industrial, medical and vehicular use.

20 Claims, 9 Drawing Sheets

Figure 1:
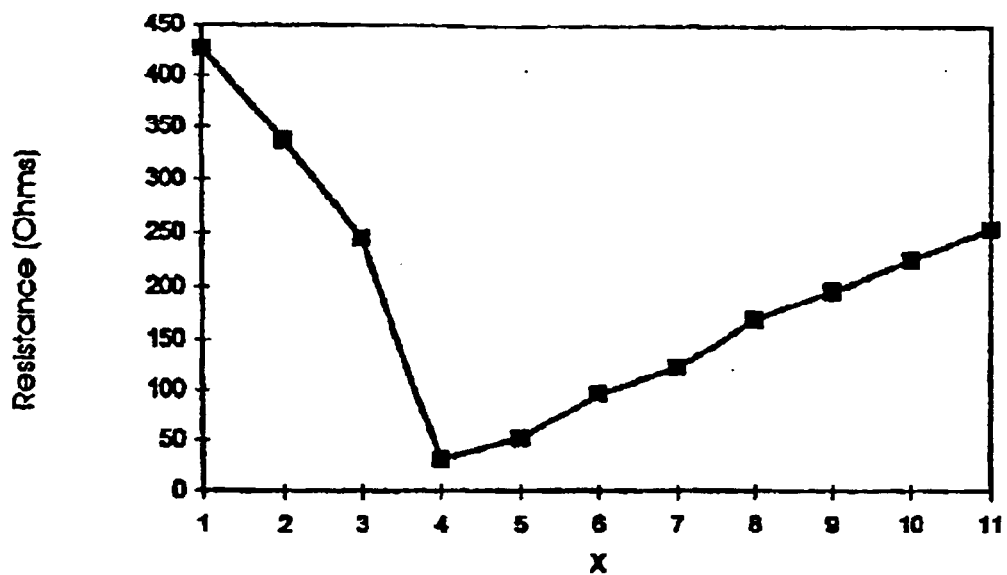

Resistance change with varying x in the system $Ni_xCo_{1-x}O_y$

OTHER PUBLICATIONS

Grace, J M., et al., "A Review Of Liquid Atomization By Electrical Means", *J. Aerosol Science*, 25 (6), (1994), 1005–1019.

Lennykh, I M., et al., "Abstract for SU 902082 Patent", *Derwent WPI Database*, (Jan. 30, 1982).

Stelzer, NHJ, et al., "Electrostatic Spray Deposition of Doped YSZ Electrode Materials for a Monolithic Solid Oxide Fuel Cell Design", *Laboratory for Applied Inorganic Chemistry, Delft Univ of Tech, Julianalaan 136, 2628 BL Delft, The Netherlands*, 236–247.

* cited by examiner

Resistance change with varying x in the system $Ni_xCo_{1-x}O_y$

CARBON MONOXIDE DETECTOR

RELATED APPLICATIONS

This application is a continuation of U.S. patent application Ser. No. 10/208,601 filed 29 Jul. 2002, which is a continuation under 35 U.S.C. 111(a) of International Application No.: PCT/GB01/00334 filed 29 Jan. 2001 and published in English under Publication No. WO 01/55710 A1 on 2 Aug. 2001, which claims priority from Great Britain Application No. 0002027.1 filed 28 Jan. 2000 and Great Britain Application No. 0002808.4 filed 9 Feb. 2000, which applications and publications are incorporated herein by reference.

The present invention relates to a method and an instrument for detecting carbon monoxide.

Carbon monoxide is an odourless, colourless, tasteless poisonous gas which can be produced by incomplete combustion of hydrocarbons. Gas fired domestic equipment such as water heaters, gas fires etc. can give off carbon monoxide when they are not functioning properly or when they are not properly maintained and checked. The emission of carbon monoxide can be fatal and there have been people killed by carbon monoxide poisoning in these circumstances, even levels of carbon monoxide below the lethal limit can cause headaches, nausea and illness due to carbon monoxide poisoning.

Apart from domestic situations, carbon monoxide can be emitted in industrial operations and is a component of the exhaust of internal combustion engines. The levels of carbon monoxide is a measure of air pollution and legal controls are imposed on carbon monoxide levels in air.

For these reasons accurate reliable carbon monoxide monitors are needed which can detect and monitor accurately low levels of carbon monoxide.

Existing types of carbon monoxide detectors can be broadly classified into one of four types according to the gas sensitive element employed: chemical, electrochemical, semiconducting or spectroscopic (infra-red). The electrochemical and spectroscopic devices, whilst offering rapid response times, high resolution and high accuracy, are expensive and not suitable for domestic use. Chemical sensors are inexpensive devices that are usually based on palladium or iodine salts which exhibit a colour change upon exposure to CO. They are of two classes; tapes for continuous monitoring which can provide very fast and sensitive response (typically sub ppm concentrations are sensed) but these require very careful control over moisture content and tubes which are used for spot checks and are of generally lower sensitivity than tapes although they do not require such careful control of moisture. Both types rely on a colour change and could not be made "automatic" by the application of an electronic device the degree of colour change. These devices are not reusable. However, their response to low CO concentrations tends to be poor and therefore constant monitoring is required and can only be used once and fail to provide audible warning signals.

The most popular carbon monoxide detectors for domestic use utilise a gas sensitive semiconductor, the resistance of which changes upon exposure to a reducing gas. Of these the most popular material is $SnO_2$ and platinum doped $SnO_2$ other binary oxides include ZnO, $TiO_2$ and a combination of CuO and ZnO to form a heterocontact More recently the use of mixed metal oxide semiconductors for CO detection has been reported. These materials include the niobates $CrNbO_4$, $FeNbO_4$ and $Ba_6Fe_{1.5}Nb_{8.5}O_{30}$ and the perovskite $La_{0.5}Sr_{0.5}CO_3$.

However, three problems exist with the use of semiconducting metal oxides for CO detection these are:
1. Low sensitivity to concentrations below approximately 100 ppm, this being equally as applicable to high operating temperatures as it is to operation at room temperature.
2. Poor selectivity towards the gas desired for detection with respect to cross sensitivity with co-existing gases.
3. Poor reproducibility of sensor characteristics, in particular due to the fabrication processes employed. The use of ESD, and related techniques, provides for greater control over fabrication and therefore sensor characteristics.

$SnO_2$ provides resistance changes upon exposure to a wide range of gases including, CO, $CH_4$ and $H_2S$. The problems of sensitivity and selectivity are commonly overcome by heating the semiconductor to approximately 200° C. for response to CO. However, such heating is considered undesirable due to the power drain being too great for remote operation from batteries and a mains power supply is necessary and sensitivity can remain poor with respect to sub 100 ppm levels even with heating to greater than 200° C.

We have now discovered a semiconducting oxide which exhibits appreciable resistance changes to CO concentrations below 100 ppm and is capable of operation at room temperature and which can be incorporated into CO detection units for domestic, industrial, medical and vehicular use.

According to the invention there is provided a method for the detection of carbon monoxide in air which comprises contacting the air with a sensor which incorporates an element formed from $Ni_xCo_{1-x}O_y$ (I) where x is from 0.1 to 0.9, and y is 4x, and measuring the change in the electrical properties of the element. Preferably, x is from 0.2 to 0.5 and y is from 0.8 to 2.0. When x is 0.33 and y is 4x a spinel structure is formed. When x is not 0.33 some spinel will be present which will be active but other oxides such as NiO and $Co_3O_4$ will also be present.

The invention also provides a device for detecting carbon monoxide levels in air, which device comprises a sensor element comprising a film or layer of (I) and a means able to measure a change in the electrical properties of the film or layer on exposure to carbon monoxide.

Preferably (I) has a spinel structure and the stoichiometric formula of (I) is $NiCo_2O_4$, i.e., x is 0.33 and y is 4x, but in practice, (I) will have a formula which can be expressed as $Ni_xCo_{1-x}O_y$ with deviation from the exact formula giving a sensor which is less effective but which could be useful. This is indicated by the change in resistance in air of the compound; the greater the resistance the greater the change in resistance being needed for a reliable detection signal and this is illustrated in FIG. 1 in which it can be seen that at X=0.33 there is the lowest resistance.

Depending on the method of formation, a film or layer of (I) will contain $NiCD_2O_4$ mixed with cobalt and nickel oxides to give a composition in which the ratio of the components deviate from the strict stoichiometric ratios.

Any electrical property which changes on contact of the film with carbon monoxide can be monitored e.g. the resistance, capacitance etc. A preferred property is the resistance and the resistance of (I) increases on exposure to carbon monoxide.

A device according to the invention which utilises the change in resistance of (I) comprises a substrate on which there is an element which comprises a film or layer of (I), attached to the element are electrodes and there is a means to measure the electrical resistance of the element. The means to measure the resistance can be any conventional means, for example a small voltage is applied between the electrodes e.g. from a battery and the current flowing monitored.

The film or layer of (I) can optionally include graphite powder, preferably in an amount of 5 to 20% of the weight of the film or layer. The graphite powder should be uniformly dispersed in the film or layer and preferably has an average particle size below one micron.

When the element is exposed to carbon monoxide the resistance of the element increases and the current decreases, when the current decreases below a pre-set level, which indicates a level of carbon monoxide above a safe level, an alarm or warning can automatically be triggered. Alternatively the change in voltage at constant current can be used to evaluate the resistance change. In addition the device can be used to provide for the continuous detection of carbon monoxide. The device can be adapted to provide for the continuous monitoring of carbon monoxide levels by means of circuitry which correlates the change in the resistance of the element with change in concentrations of carbon monoxide.

If the power supply should fail, a warning or alarm is automatically triggered as the current drops and this a fail-safe feature against inoperation due to power failure.

In order to measure the resistance there are electrodes attached to the film or layer of (I) and it is important that there is a good electrical contact between the film and the electrodes so there is minimal resistance caused by the attachment of the electrodes to the element.

Preferred electrodes can be formed of an inert metal such as gold, which has no electrical junction effects with the sensor element. The contact material itself should have no reaction with carbon monoxide.

In order to compensate for the effect on resistance of temperature fluctuations a reference sensor can be used which is the same as the detecting sensor but which is hermetically sealed from the atmosphere and so sealed from the sensing environment. Both the sensors would be subject to the same temperature fluctuations and so any difference in their resistances would be due solely to the presence of a reacting gas.

As changes in the electrical resistance of the element are measured, a low base resistance of the element is preferred so the change in resistance of the element compared with the base resistance of the element is greater. This can be accomplished by having an element with a low specific resistivity and there being a short path length through the element between the electrodes. The resistance change required to give a reliable signal will depend on the particular circumstances and the electrical circuits used, but normally a resistance change of 25% is suitable although lower resistance changes can be used, particularly when a reference sensor is used to compensate for temperature variation.

The film or layer of (I) can be prepared by known methods for example by thermal decomposition of solutions of the metal nitrates or hydroxides, spray pyrolysis, cryochemical deposition, co-precipitation of the metal oxides and electrostatic spray deposition.

The preferred methods used are thermal decomposition and electrostatic spray deposition. However a printing technique, such as silk screen printing may also be applied using $NiCO_2O_4$ powder and a solution of metal salts followed by thermal decomposition.

Electrostatic spray deposition is described in "A Review of Liquid Atomisation by Electrical Means" by J. M. Grace and J. C. M. Marijinissen, ESF Workshop on Electrospraying. Sevilla 1997 and "Electrostatic Spray Deposition of Doped YSZ Electrode Materials for a Monolithic Solid Oxide Fuel Cell Design" 10th IEA SOFC Workshop. Diablerets. Switzerland. 2 (1997) 236–247.

A preferred structure of the sensor of the present invention has a film of (I) deposited or formed on to a substrate such as foil or ceramic substrate. Preferably a film of (I) is deposited on the substrate as it is formed e.g. by thermal decomposition of solutions of precursor metal salts such as metal nitrates or by electrostatic spray deposition e.g. of precursor metal salts such as metal nitrates.

The nature of the substrate is not critical and any suitable substrate can be used, for example substrates which have physical properties similar to those of the deposited film.

When thermal decomposition is used to form the film or layer, mixed cobalt and nickel nitrates are preferably thermally decomposed directly onto a substrate such as a nickel foil. Nickel has a coefficient of expansion similar to (I) so the risk of cracking etc. due to changes in temperature is reduced. The film or layer can be made by forming a gel of cobalt nitrate and nickel nitrate in stoichiometric ratio by evaporation of a solution of the mixed nitrates on the substrate and then drying and heating the gel at elevated temperature for example from 250° C. to 650° C. e.g. 350° C. to form the film or layer of compound (I) on the substrate.

The technique of Electrostatic Spray Deposition (ESD), developed at the University of Delft, provides an inexpensive and facile means of preparing thin films of inorganic substances. ESD has been successfully applied to production of a wide variety of thin films for solid oxide fuel cells, including those having a spinel structure.

ESD involves the production of an aerosol from a precursor solution through the application of a high positive potential to a metal capillary (nozzle), this being directed towards a heated, electrically grounded substrate. As the precursor solution is pumped through the capillary, droplets will grow at the tip of the nozzle.

The positive potential causes positive ions in the solution to migrate to the surface the droplet, resulting in a surface charge which causes an electrostatic pressure to oppose the surface tension of the liquid. Through the variation of electrode configuration, nozzle design and liquid properties (viscosity and conductivity) many spray modes, having widely different geometries, may be achieved.

A process of decomposition then occurs as charged droplets are subsequently attracted by coulombic forces to the grounded substrate. It is suggested that such decomposition occurs, together with solid state reaction of precursor cations, within the spray cone caused by the high potential being applied Conventional ESD can be used in the present invention. Other techniques which can be used include flame assisted vapour deposition and electrostatically assisted vapour deposition.

Another method of preparing $NiCo_2O_4$ films onto metal substrates is by co-spraying $NiCo_2O_4$ films powder and solution together via electrostatic spraying or simply depositing the mixture and solution onto the substrate followed by thermal decomposition e.g. at 400° C. or by use of printing techniques.

It is a feature of the sensors of the present invention that they are resistant to interference by other pollutant gases which are commonly present in the atmosphere such as oxides of nitrogen, referred to as NOx, and the sensors of the present invention work in the presence of such gases.

In general the sensors work better at higher temperatures, but unlike existing sensors the sensors of the present invention detect low levels of carbon monoxide at ambient temperatures. The sensors of the present invention are also relatively unaffected by changes in humidity.

The performance of the sensors of the present invention can be affected by the addition of other metals as surface and bulk additives to the compound (I). It was found that the addition platinum group metals e.g. palladium could improve the sensitivity, the levels of palladium used preferably range from 1 to 5% preferably 4 to 5%.

The invention is illustrated in the following Examples.

EXAMPLE 1

Nickel foil (99.9% Aldrich) had a film of (I) formed on it by a process in which the foil substrate was coated three times with mixed cobalt and nickel nitrates from an alcoholic solution, pressed under a 1 kg weight to equalise particle separation and obtain uniformity of coverage and then fired at 400° C. for 2 hours between each successive coating. The loading thereby obtained was 3.2 g/cm$^2$. The resistance was then measured along a linear profile on each surface via a two probe method using a digital multimeter (Hewlett Packard 3478A) and the contact spacing measured to two decimal places with a digital micrometer (Mitayoka). The relationship between resistance and contact spacing was observed to be linear.

The sensors were evaluated for their response to carbon monoxide. Sensitivity is defined as ($R_g$-Ro)/Ro where $R_g$ is the resistance in the contaminant gas and Ro is the resistance in clean air.

A change in resistance of 25% was arbitrarily taken as a level which would be used to trigger an alarm. The sensor was exposed to air containing various levels of carbon monoxide and the time taken to register a 25% change in resistance measured.

In exposure to air free of carbon monoxide the variation in resistance over a long period of time (72 hours) was found to vary between 0.25 and 0.6% of the initial value and in exposure to air with background levels of carbon monoxide (1 ppm) the resistance was found to vary by −1.4 to +3.5% of the initial value thus indicating that there was little risk of false positives being found.

Figure 2:
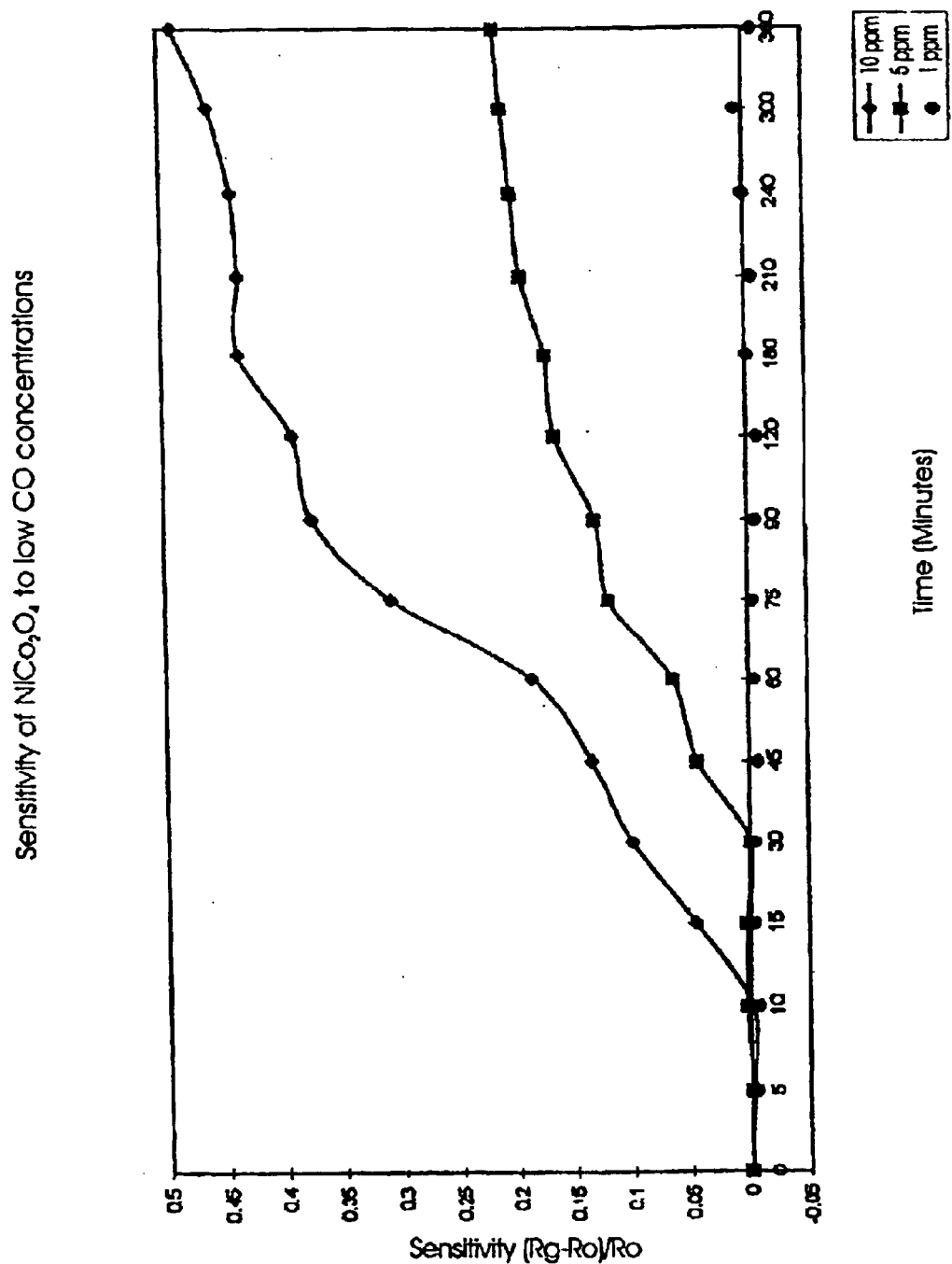

The sensor was exposed to a carbon monoxide concentration of 10 ppm and the resistance measured against time, a change in sensitivity of 3 indicates a 25% change in resistance. The results and the result for exposure to background level of 1 ppm carbon monoxide is shown in FIG. 2, as can be seen the warning level was attained after 75 mins. Existing semiconductor sensors cannot detect carbon monoxide levels of this order at ambient temperatures.

Figure 3:
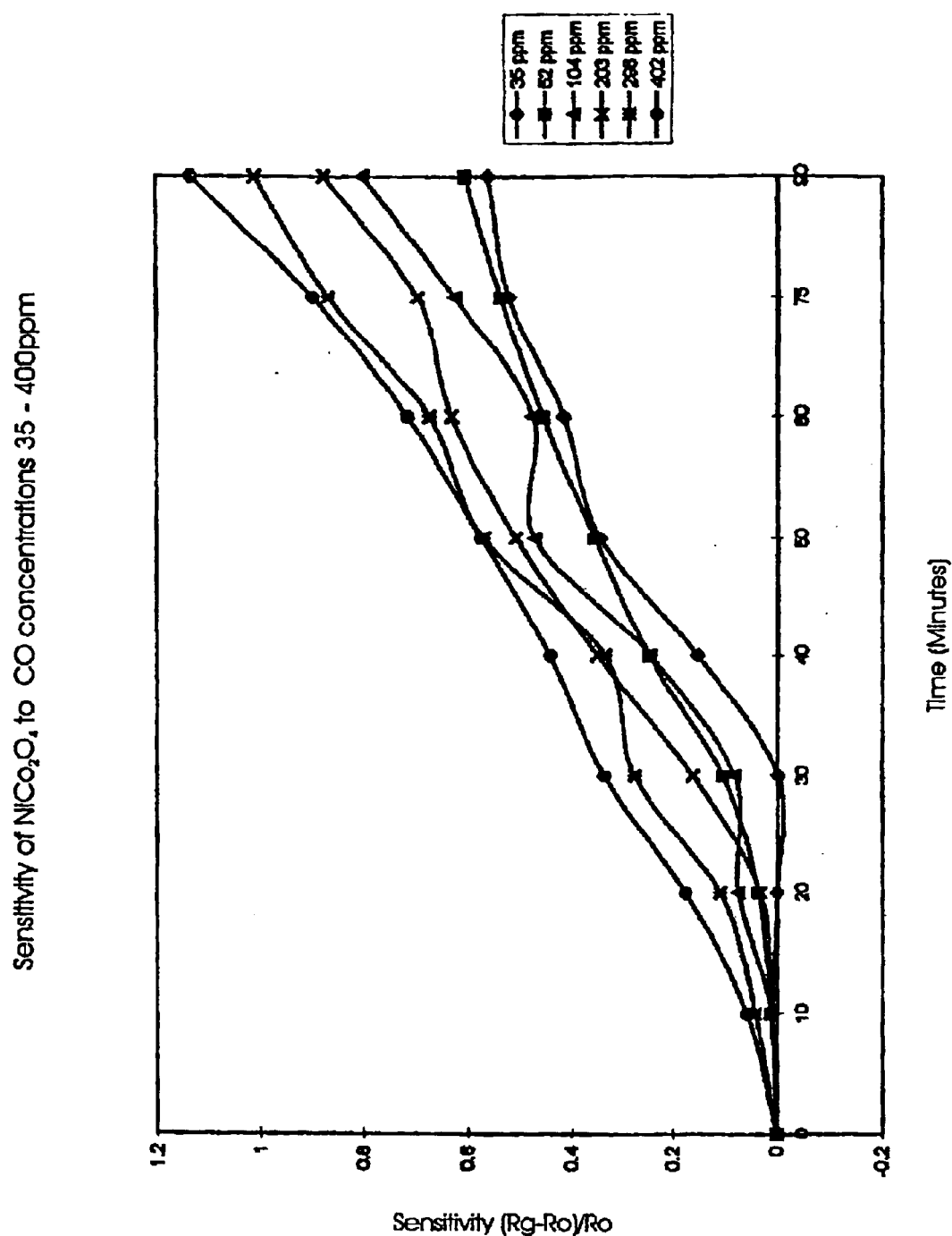
Figure 4:
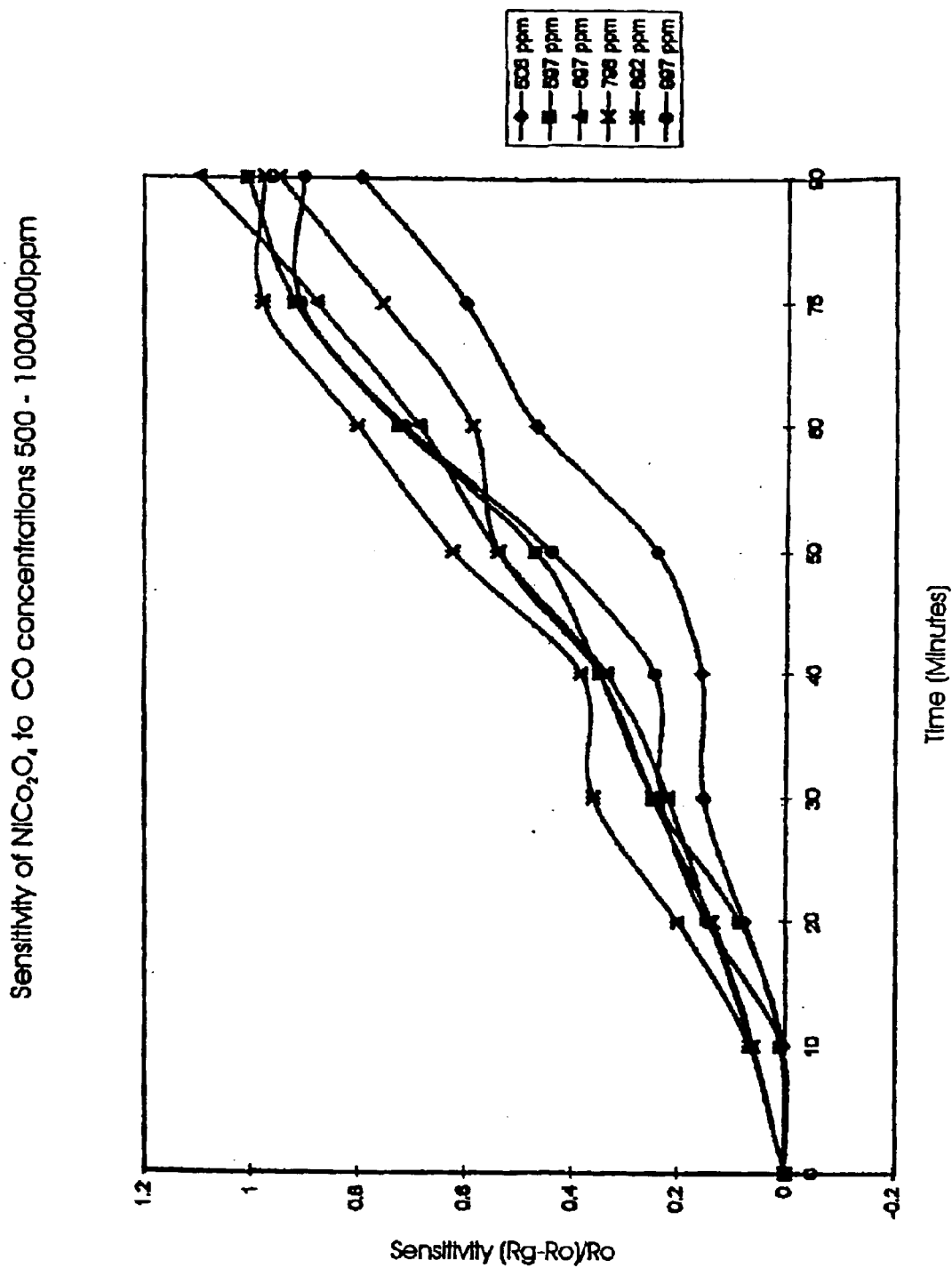
Figure 5:
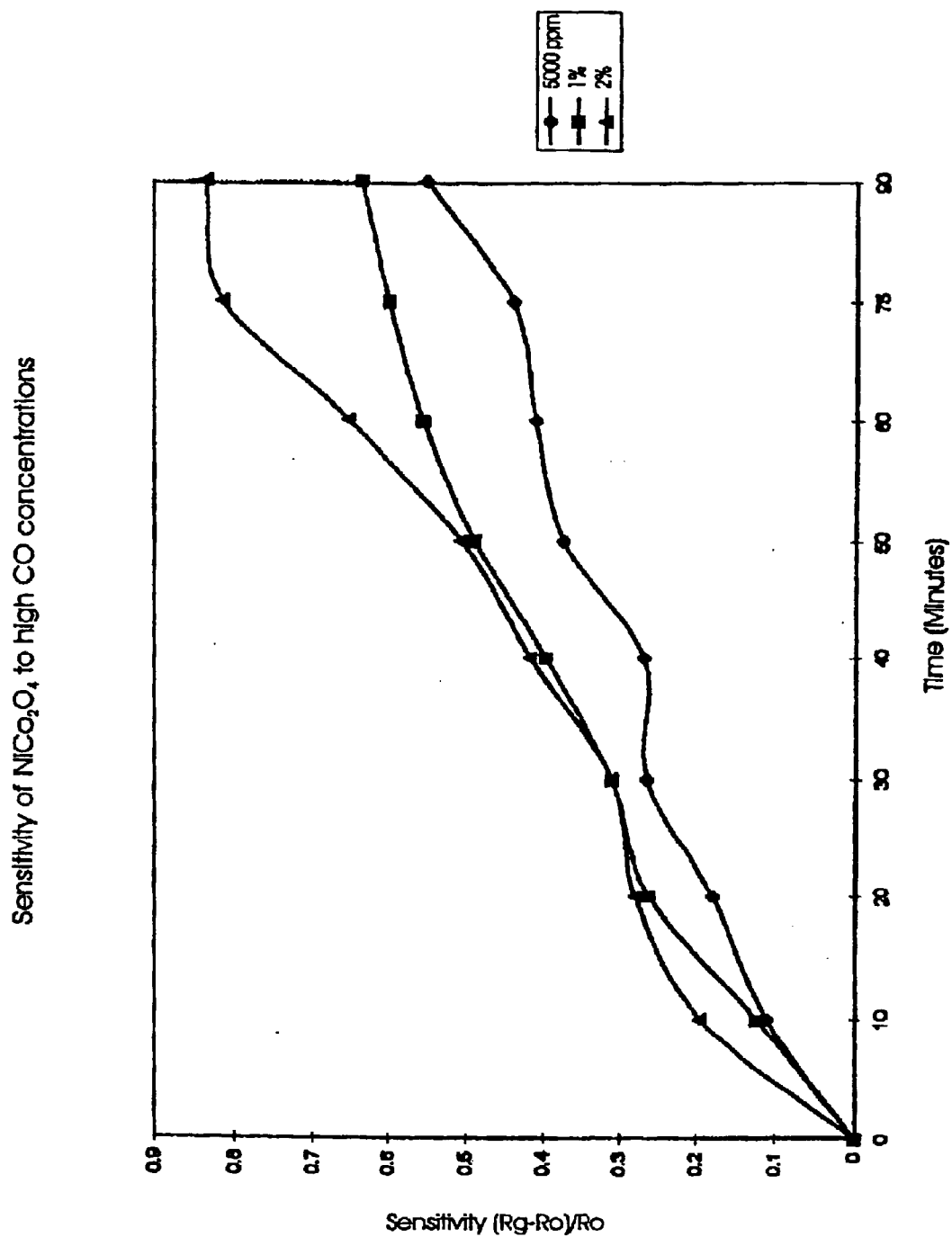

This was repeated for carbon monoxide concentrations of 35 ppm to 400 ppm, 500 to 1000 ppm and for 5000 ppm to 2% and the results shown in FIGS. 3, 4 and 5.

Figure 6:
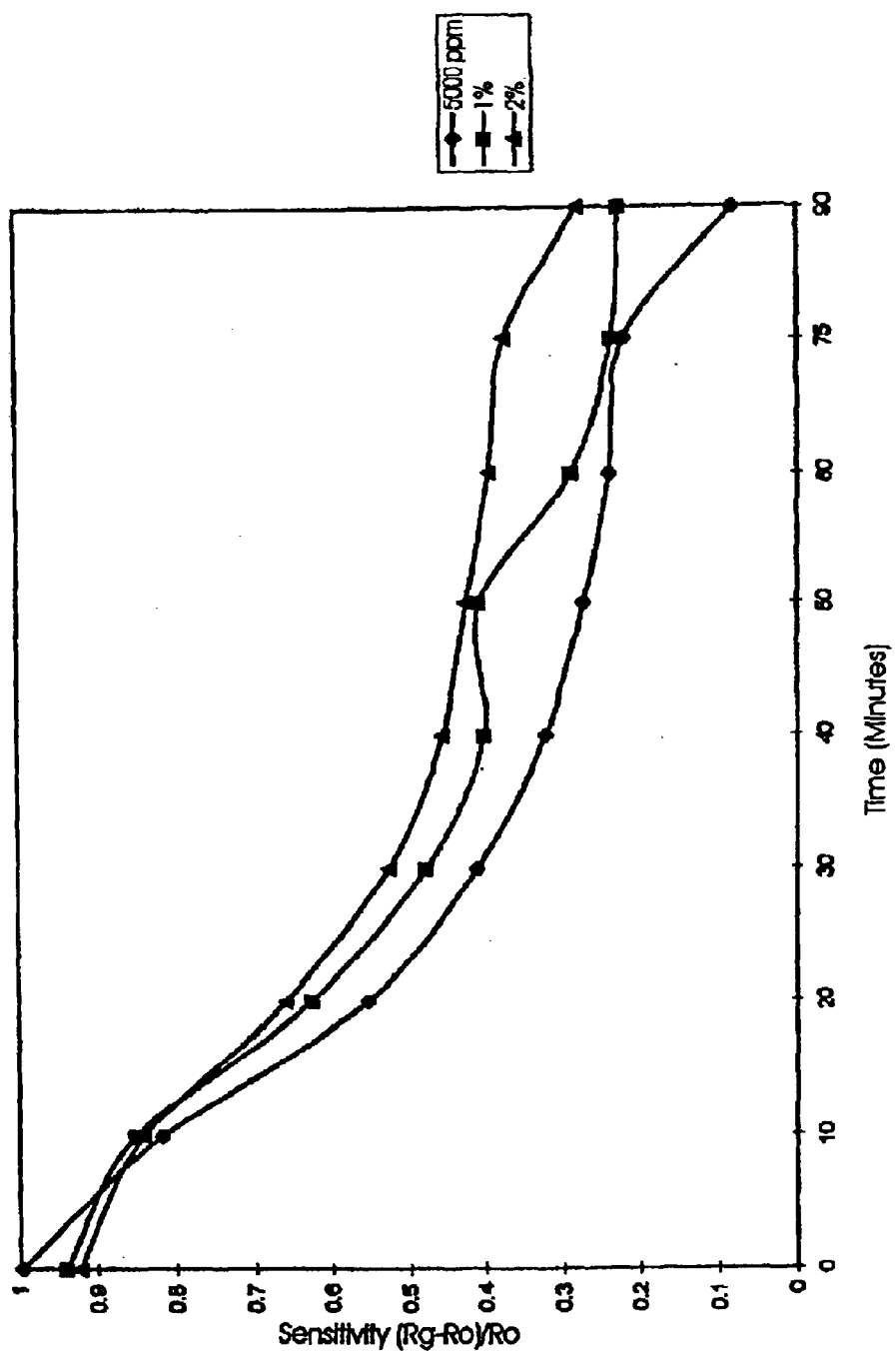
Figure 7:
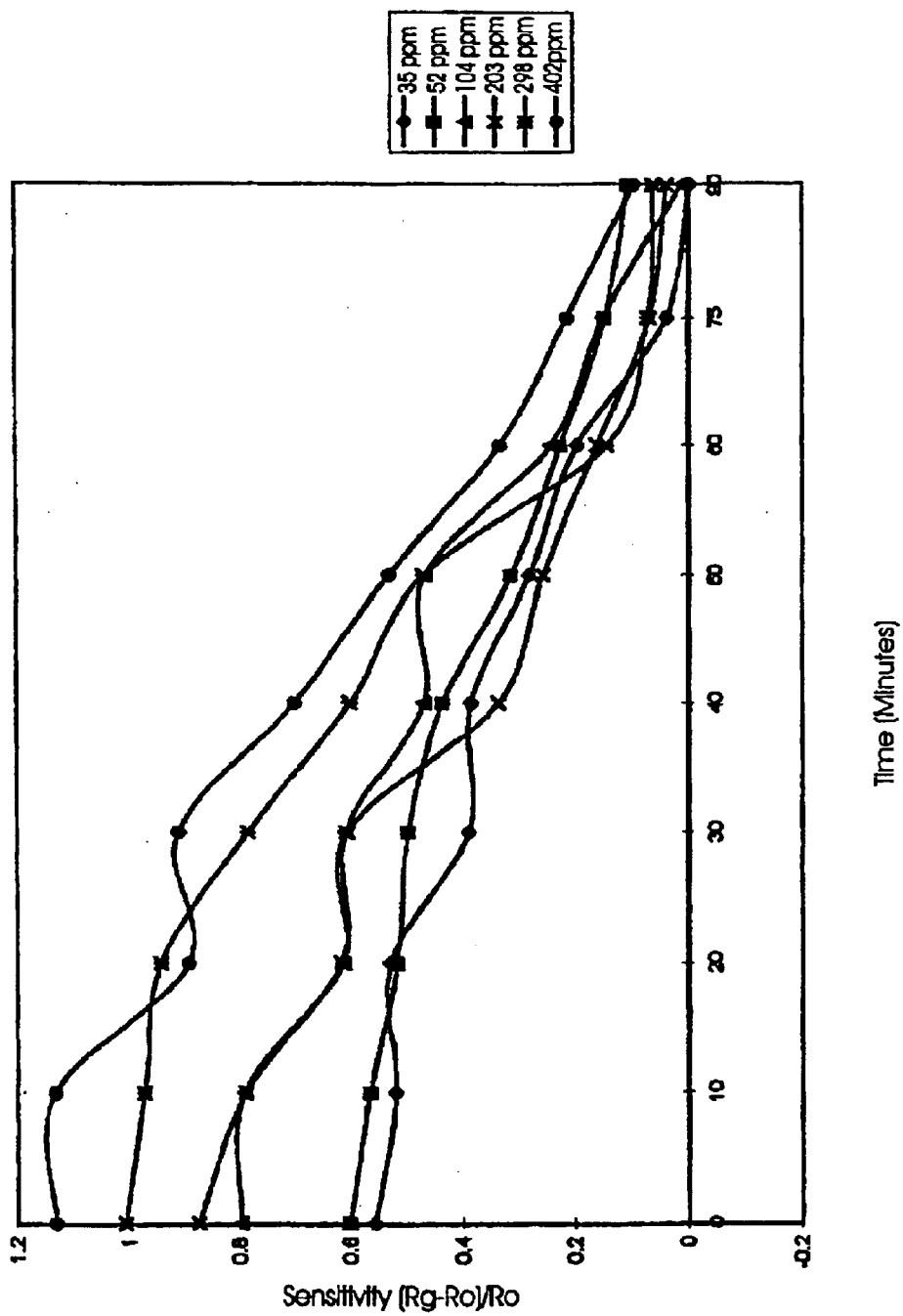
Figure 8:
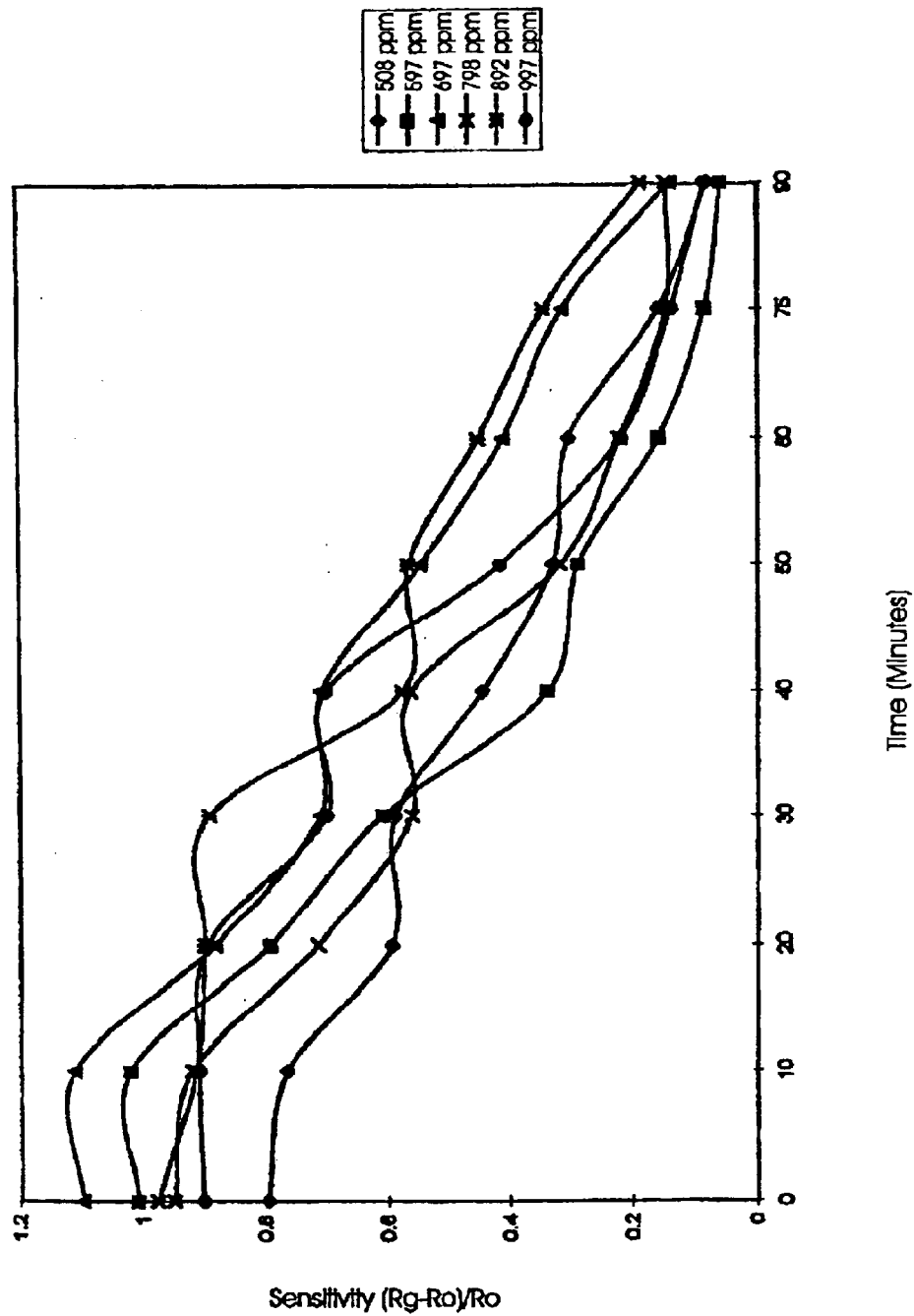

The recovery of the sensor when the levels of carbon monoxide were reduced to background levels was also measured and the results shown in FIGS. 6, 7 and 8. As can be seen the resistance was quickly reduced to its base level.

The sensors were evaluated for sensitivity to NOx as a pollutant gas which is found some exhaust gases which contain carbon monoxide and it was found that there was no decrease to the selectivity to carbon monoxide on exposure to NOx in the concentrations likely to be found.

EXAMPLE 2

Electrostatic Spray Deposition

Figure 9:
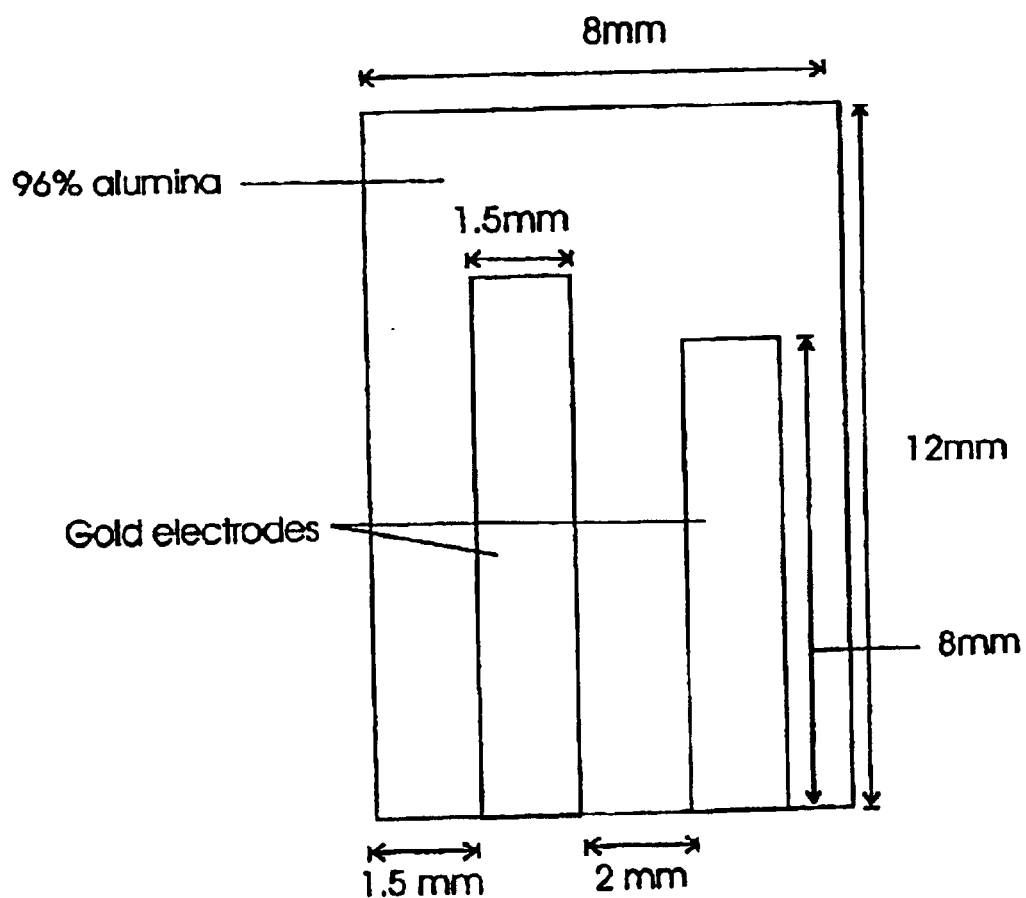

A ceramic substrate of 96% alumina having screen printed gold electrodes (Du Pont plc) was cut to the dimensions shown in FIG. 9 which illustrates an example of a sensor substrate coated with NiCo$_2$O$_4$ using electrostatic spray deposition under a range conditions to prepare a number of samples and the conditions used are shown in Table 1.

TABLE 1

| Sample mg/cm$^2$ | Precursor flow rate ml/hr. | Precursor Molarity M | Substrate Temperature ° C. | Deposition Time hours | Applied Potential kV | Loading |
|---|---|---|---|---|---|---|
| 1 | 0.55 | 0.05 | 375 | 4 | 17.77 | 0.5 |
| 2 | 0.57 | 0.05 | 493 | 2 | 10.47 | 0.27 |
| 5 | 0.55 | 0.05 | 445 | 2 | 15.75 | 0.29 |
| 6 | 0.57 | 0.05 | 402 | 2 | 12.20 | 0.3 |
| 7 | 0.55 | 0.05 | 445 | 1 | 15.57 | 0.11 |
| 8 | 0.57 | 0.05 | 448 | 4 | 11.87 | 0.54 |
| 9 | 0.55 | 0.05 | 303 | 4 | 17.31 | 0.48 |
| 10 | 0.57 | 0.025 | 400 | 2 | 10.39 | 0.13 |
| 14 | 0.55 | 0.025 | 349 | 2 | 17.6 | 0.17 |
| 15 | 0.57 | 0.025 | 373 | 2 | 9.82 | 0.14 |
| 16 | 0.55 | 0.05 | 393 | 2 | 17.19 | 0.29 |
| 17 | 0.57 | 0.025 | 372 | 2 | 10.23 | 0.14 |

The Solvent was 20 vol % absolute alcohol and 80 vol % butyl carbinol (Di(ethylene glycol)butyl ether, (99% Aldrich).

The resistance of the samples and the sensitivity to carbon monoxide levels of 100 ppm for 1 hour as shown by the response time to achieve a 25% increase in resistance were measured as described in Example 1 and the results shown in Table 2

TABLE 2

| Sample | Response Time Mins. | Base Resistance k ohms |
|---|---|---|
| 1 | 60 | 1.52 |
| 2 | 45 | 4.24 |
| 5 | 20 | 4.20 |
| 6 | 50 | 2.88 |
| 7 | 20 | 4.36 |
| 8 | 30 | 2.22 |
| 9 | 20 | 1.40 |
| 10 | 40 | 2.52 |
| 14 | 30 | 4.60 |
| 15 | 30 | 2.44 |
| 16 | 30 | 1.12 |
| 17 | 20 | 0.28 |

As can b seen the sensors of the present invention can detect carbon monoxide from low levels at ambient temperatures.

EXAMPLE 3

Sensor samples prepared using spray pyrolysis with and without the addition of 5% palladium and the percentage increase in resistance after 30 mins exposure time to 100 ppm of carbon monoxide was measured at temperatures from 50° C. to 200° C. and the results shown in Table 3 which show sensitivity values.

TABLE 3

| Sensor | 50° C. | 100° C. | 150° C. | 200° C. |
|---|---|---|---|---|
| NiCo$_2$O$_4$ | 9 | 7 | 10 | 13 |
| NiCo$_2$O$_4$ + Pd | 8 | 18 | 26 | 36 |

As can be seen the addition of the palladium increases the sensitivity.

What is claimed:

1. A device for monitoring carbon monoxide levels in air, wherein the device includes a sensor element having a film or layer comprising $Ni_xCo_{1-x}O_y$, where x is from 0.1 to 0.9 and y is 4x; wherein when carbon monoxide is detected, the resistance of the sensor element increases and the current through the sensor element decreases; and the device triggers an alarm or warning when the current decreases below a predetermined level.

2. The device of claim 1 wherein x is from 0.2 to 0.5 and y is from 0.8 to 2.0.

3. The device of claim 2 wherein the sensor element comprises $NiCo_2O_4$.

4. The device of claim 2 wherein the sensor element consists essentially of $NiCo_2O_4$.

5. The device of claim 1 wherein the sensor element includes a substrate comprising a film or layer of $Ni_xCo_{1-x}O_y$ and electrodes attached to the film or layer.

6. The device of claim 5 wherein the film or layer consists essentially of $NiCo_2O_4$.

7. The device of claim 6 wherein the electrodes are gold.

8. The device of claim 7 wherein a voltage is applied to the sensor element and the current flow is monitored.

9. The device of claim 5 wherein the film or layer is formed by thermal decomposition of solutions of the metal nitrates onto a substrate.

10. The device of claim 9 wherein the metal nitrates comprise a mixture of cobalt and nickel nitrates.

11. The device of claim 10 wherein the film or layer is made by forming a gel of cobalt nitrate and nickel nitrate in a stoichiometric ratio by evaporation of a solution of the mixed nitrates on the substrate and drying and heating the gel at from 250° C. to 650° C. to form a film or layer having the formula $Ni_xCo_{1-x}O_y$ on the substrate.

12. The device of claim 11 wherein the substrate is nickel foil.

13. The device of claim 11 wherein the film or layer is formed by electrostatic spray deposition.

14. The device of claim 1 wherein when the level of carbon monoxide exceeds a predetermined level, the device emits an alarm or warning.

15. The device of claim 11 wherein the film or layer further comprises palladium as a surface or bulk additive.

16. The device of claim 15 wherein the sensor element comprises 1 to 5% palladium by weight.

17. The device of claim 11 wherein the sensor element is a film or a layer and comprises graphite powder.

18. The device of claim 17 wherein the sensor element comprises 5 to 20% graphite powder by weight; and wherein the graphite powder has an average particle size less than one micron.

19. The device of claim 1 wherein the change in the current passing through the sensor element is continuously monitored and displayed as a record of carbon monoxide levels.

20. The device of claim 1 further comprising a reference sensor element.

* * * * *